United States Patent [19]
Senaratne et al.

[11] Patent Number: 5,902,906
[45] Date of Patent: May 11, 1999

[54] ALKANETHIOLATION PROCESS

[75] Inventors: K. Pushpananda A. Senaratne; Charles R. Everly; Won S. Park, all of Baton Rouge, La.

[73] Assignee: Albemarle Corporation, Richmond, Va.

[21] Appl. No.: 08/847,093

[22] Filed: May 1, 1997

[51] Int. Cl.$^6$ .................................................. C07C 319/14
[52] U.S. Cl. .............................................................. 568/38
[58] Field of Search ................................................ 568/38

[56] References Cited

U.S. PATENT DOCUMENTS

| | | | |
|---|---|---|---|
| 2,923,743 | 2/1960 | Delfs et al. | 260/609 |
| 4,594,453 | 6/1986 | Ranken et al. | 564/440 |

FOREIGN PATENT DOCUMENTS

| | | | |
|---|---|---|---|
| 8245558 | 9/1996 | Japan . | |

OTHER PUBLICATIONS

Database Chemabs Abstract of Russian journal article, Yushko, et al., "Formation of aryl alkyl and diaryl sulfides under alkylation conditions", Vopr. Khim, Khim Tekhnol., 1994, vol. 32, pp. 18–22.

Abstract of JP 08 245 558, 1996.
Abstract of JP 49 054 338, 1974.
Ranken et al., J. Org. Chem., 1989, 54(12), pp. 2985–2988, Dec. 1989.
Mukaiyama et al., Chemistry Letters, 1993, 1, pp. 1–4, Jan. 1993.
Matsumoto et al., J. Chem. Research, 1995, 1, 34–35, Jan. 1995.

*Primary Examiner*—Richard Raymond
*Assistant Examiner*—Brenda Coleman
*Attorney, Agent, or Firm*—Philip M. Pippenger

[57] ABSTRACT

A mixture formed from one or more alkyl disulfides, benzene, and at least about 1.5 equivalents of Lewis acid catalyst is heated to form alkanethiobenzene. Reaction in a mixture formed from excess benzene, dimethyldisulfide (DMDS) and $AlCl_3$ in which the mole ratio of $AlCl_3$ to DMDS was 2:1 was complete in 2 hours and afforded 98% conversion and 93% yield of thioanisole. In contrast, the same reaction when attempted using a 1:1 mole ratio of $AlCl_3$ to DMDS after 6 hours achieved only 66% conversion and a thioanisole yield of only 35%. So far as is known, this is the first example of a highly efficient electrophilic aromatic substitution of the inactivated benzene ring by an alkanethio group.

20 Claims, No Drawings

ALKANETHIOLATION PROCESS

TECHNICAL FIELD

This invention relates to an alkanethiolation process enabling efficient production of thioanisole and its higher alkyl homologs directly from benzene.

BACKGROUND

Thioanisole is a useful pharmaceutical intermediate. A known method for production of thioanisole involves methylation of thiophenol with methyl chloride in aqueous base. Hiroshi, I. et al., Japan Kokai Tokkyo Koho 94-95830, April, 1994. However, thiophenol is a costly raw material for thioanisole production.

A variety of other synthetic reactions for certain arylalkylsulfides are known. See for example, Barrett, G. C. "Sulfides" in *Comprehensive Organic Chemistry*, Edited by Barton and Ollis, Pergamon Press, 1979, and references cited therein. These include: Lewis acid catalyzed alkanethiolation of arenes using dimethyldisulfide or its derivatives, nucleophilic aromatic substitution of aryl halides with alkanethiolate salt, acid catalyzed alkanethiolation of aryl alcohols using alkane thiols, Pd-catalyzed alkanethiolation of arylhalides with alkane thiols, nucleophilic aromatic substitution of alkanethiolate with diazonium salt of arylamines, etc. Many of these alkanethiolation reactions work well with activated arenes such as phenols or anilines, but have not proven suitably effective for alkanethiolation of inactivated benzene itself. Indeed, only a few examples of thioanisole synthesis from benzene are known. For example, in Brintzingher, L., *Chem. Ber.* 1953, 86, 557, 562, it is shown that methanethiolation of benzene with methanesulfenylchloride in the presence of one equivalent of $AlCl_3$ produced a yield of about 50%. Xylene and mesitylene were methanethiolated with methanethiosulfonate in the presence of one equivalent of $AlCl_3$, but not benzene or toluene. See Kloosterziel, H. et al., *Chem. Comm.*, 1971, 1365. It appears that there have been no synthetic reactions reported enabling efficient alkanethiolation of benzene. This invention provides such a process.

THE INVENTION

This invention provides, inter alia, a new, efficient synthesis of thioanisole from benzene and dimethyldisulfide (DMDS) with high yield and conversion. Moreover, the process can be applied to synthesis of thioethers of the formula

where R is an alkyl group having up to about 15 carbon atoms, and preferably up to about 10 carbon atoms, again by use of benzene as a reactant in the process.

Making these new results possible, is the discovery that the reaction between benzene and a dialkyldisulfide is highly efficient if the reaction is performed in the presence of at least 1.5 equivalents of a Lewis acid, preferably $ALCl_3$, per mole of the disulfide. Preferably, at least 2 equivalents of Lewis acid per mole of the disulfide. For example, it has been found that reaction in a mixture formed from benzene, DMDS and $AlCl_3$ in which the mole ratio of $AlCl_3$ to DMDS was 2:1 was complete in 2 hours and afforded 98% conversion and 93% yield of thioanisole. In contrast, the same reaction when attempted using a 1:1 mole ratio of $AlCl_3$ to DMDS after 6 hours achieved only 66% conversion and a thioanisole yield of only 35%. So far as is known, this is the first example of a highly efficient electrophilic aromatic substitution of the inactivated benzene ring by an alkanethio group.

As known in the chemical arts, a chemical reaction is caused by mixing or contacting the required ingredients with each other in the amounts and under conditions effective to bring about the desired reaction. What actually takes place in the reaction mixture is a matter of chemical theory, as no one can actually see what is really going on at the molecular or sub-molecular level in the reaction mixture.

Disulfides of the formula, RSSR, where R is alkyl group of up to about 15 carbon atoms (preferably, up to about 10 carbon atoms), can be used in the practice of this invention. Each alkyl group is most preferably a primary alkyl group. Dimethyldisulfide is the most preferred reactant.

Suitable Lewis acids include $AlCl_3$, $AlBr_3$, $ZnCl_2$, $FeCl_3$, $BF_3$, $SnCl_4$, and like substances. Of these, $AlCl_3$ is most preferred.

The reaction should be conducted at one or more temperatures in the range of about 25° C. to about 200° C., and preferably about 25° C. to about 82° C., using an excess of benzene as the reaction medium. Typically, the mole ratio of benzene to the disulfide should be at least about 5:1 and preferably 10:1 or more. At temperatures above about 82° C. the reaction should be conducted in a closed reaction system under superatmospheric pressure(s). Preferably the mixture is heated to reflux temperature(s) at ordinary atmospheric pressure(s). While amounts of Lewis acid well in excess of 2 equivalents per mole of the disulfide reactant can be used, it is desirable to keep the proportions in the range of about 2 to about 5 equivalents of Lewis acid per mole of the disulfide.

EXAMPLE

The practice and advantages of this invention were demonstrated by conducting reactions of benzene with DMDS in the presence of $AlCl_3$ at a refluxing temperature of benzene using it as a solvent and a reactant. The desired reaction may be represented by Eq. 1 as follows:

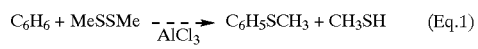

The general procedure used for the practice of this invention was as follows: To a 250 mL 3-necked round-bottomed flask equipped with a Friedrichs condenser connected to a caustic trap and a bleach solution trap in series, a mechanical stirrer, and an addition funnel attached to a nitrogen inlet adaptor, was placed 89.4 mL (100 mmol) of benzene and 26.7 g (20 mmol) of $AlCl_3$. A measured amount of n-decane was added to the resultant slurry as a GC internal standard (ca. 0.2 g). The mixture was heated with stirring at 82° C. and DMDS (9.0 mL, 10 mmol) was added slowly (ca. 10 min) via an addition funnel. As soon as the addition is complete, aliquots of the reaction mixture were taken periodically and worked up for GC analyses. Each sample was washed with 2% caustic solution, then with water, and the organic layer was dried on an anhydrous sodium carbonate. Then the organic solution was analyzed on a GC equipped with a DB-1 capillary column at a condition programmed for analyses of DMDS and thioanisole with response ratio correction factors. The same general procedure was used in comparative runs except that the amount of $AlCl_3$ was either 10 mole % (i.e., the mole ratio of $AlCl_3$ to DMDS was 0.1:1) or 100 mole % (where the mole ratio of $AlCl_3$ to DMDS was 1:1).

The results are summarized in Tables 1–3, wherein "Conv." is conversion, "PS" is polysulfides, and "High MW Compds." is high molecular weight compounds.

TABLE 1

Results per the Invention (AlCl$_3$:DMDS = 2:1)

| Time | % Conv. of DMDS | % Yield | % Yield on DMDS Converted | Area % Yield, PS | Area % High MW Cmpds. |
|---|---|---|---|---|---|
| 5 min. | 71.5 | 67.3 | 94.1 | 0.02 | 1.30 |
| 1 hr. | 95.3 | 88.2 | 92.5 | 0.14 | 1.36 |
| 2 hr. | 98.0 | 91.5 | 93.4 | 0.42 | 1.82 |

TABLE 2

Results Not of the Invention (AlCl$_3$:DMDS = 1:1)

| Time | % Conv. of DMDS | % Yield | % Yield on DMDS Converted | Area % Yield, PS | Area % High MW Cmpds. |
|---|---|---|---|---|---|
| 1 hr. | 48.3 | 18.8 | 38.9 | 0.6 | 4.0 |
| 3 hr. | 64.9 | 35.9 | 56.1 | 0.9 | 12.7 |
| 6 hr. | 65.9 | 34.5 | 52.4 | 0.7 | 7.9 |

TABLE 3

Results Not of the Invention (AlCl$_3$:DMDS = 0.1:1)

| Time | % Conv. of DMDS | % Yield | % Yield on DMDS Converted | Area % Yield, PS | Area % High MW Cmpds. |
|---|---|---|---|---|---|
| 1 min. | 4 | 0.03 | 0.7 | 0.84 | 0.09 |
| 5 min. | 3 | 0.05 | 1.7 | 0.87 | 0.04 |
| 30 min. | 4 | 0.14 | 4.7 | 1.03 | 0.06 |
| 45 min. | 4 | 0.22 | 5.5 | 1.12 | 0.08 |
| 1 hr. | 3 | 0.31 | 10.3 | 1.24 | 0.07 |
| 2 hr. | 7 | 0.68 | 9.7 | 1.78 | 0.14 |
| 3 hr. | 6 | 1.00 | 16.7 | 2.35 | 0.15 |
| 4 hr. | 8 | 1.27 | 15.9 | 2.88 | — |
| 5 hr. | 10 | 1.44 | 14.4 | 3.38 | 0.72 |
| 6 hr. | 8 | 1.58 | 19.5 | 3.91 | 0.74 |
| 7 hr. | 8 | 1.60 | 20.0 | 4.20 | 1.00 |
| 8 hr. | 12 | 1.63 | 13.6 | 4.64 | 1.34 |
| 9 hr. | 15 | 1.62 | 10.8 | 4.77 | 1.46 |
| 24 hr. | 30 | 0.67 | 2.2 | 4.91 | 2.86 |

When only 10 mole % of AlCl$_3$ was used (Table 3), the reaction provided a <2% maximum yield of thioanisole in about 8 hours and then the yield started to decrease. Even when one mole equivalent of AlCl$_3$ was used (Table 2), the maximum yield was but 46% (69% based on conversion) in about six hours, and thereafter the yield slowly decreased by conversion of thioanisole to high molecular weight material presumably via redistribution processes. It appeared that two reaction steps were involved: (1) thioanisole formation, and (2) conversion of thioanisole to higher molecular weight compounds. In sharp contrast, in the process of this invention where two mole equivalents of AlCl$_3$ were used relative to the DMDS (Table 1), the reaction was very rapid and selective. After only 5 minutes over 70% of the DMDS was converted and the yield of thioanisole was 94.2% based on the converted DMDS. Moreover, after two hours the reaction had proceeded substantially to completion providing a high conversion and yield.

These experiments indicate that in order to accelerate the first step, large excesses of benzene (5–10 fold or more) are helpful. Without desiring to be bound by theory, it is believed that the MeSH byproduct and thioanisole product each form complexes with AlCl$_3$. Therefore, it is theorized that if less than one equivalent of Lewis acid such as AlCl$_3$ is used relative to the DMDS, the complexed Lewis acid is incapable of catalyzing the desired reaction, and there is little, if any, free Lewis acid to exert such catalytic effect. On the other hand, in the process of this invention free Lewis acid appears available to exert the catalytic effect on the desired reaction. Further, it is believed that by quickly being consumed for the first step of the reaction, the DMDS becomes unavailable for the second step of multi-substitution reactions which normally would lead to co-product formation such as polysulfides and high molecular weight species. For example, the short reaction time required in the runs of this invention apparently decreased disproportionation of thioanisole to benzene and bis-methanethiolated benzene.

So far as is presently known, this is the first example of achieving such high yields and conversions in Lewis acid catalyzed methanethiolation of inactive benzene with DMDS via electrophilic aromatic substitution.

It is to be understood that the reactants and components referred to by chemical name or formula anywhere in the specification or claims hereof, whether referred to in the singular or plural, are identified as they exist prior to coming into contact with another substance referred to by chemical name or chemical type (e.g., another reactant, a solvent, or etc.). It matters not what preliminary chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. Thus the reactants and components are identified as ingredients to be brought together in connection with performing a desired chemical reaction or in forming a mixture to be used in conducting a desired reaction. Accordingly, even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients in accordance with the present disclosure. The fact that a substance, component or ingredient may have lost its original identity through a chemical reaction or transformation during the course of contacting, blending or mixing operations, if conducted in accordance with this disclosure and with the application of common sense and the ordinary skill of a chemist, is thus wholly immaterial for an accurate understanding and appreciation of the true meaning and substance of this disclosure and the claims thereof.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

What is claimed is:

1. A process which comprises subjecting a mixture formed from ingredients comprising (i) at least one disulfide of the formula RSSR where each R is, independently, an alkyl group having up to about 15 carbon atoms, (ii) benzene, and (iii) at least about 1.5 equivalents of Lewis acid per mole of the disulfide used in forming the mixture, to conditions effective to form a compound of the formula $RSC_6H_5$ where R is an alkyl group having up to about 15 carbon atoms, such that said compound of the formula $RSC_6H_5$ is formed.

2. A process in accordance with claim 1 wherein the Lewis acid used in forming said mixture is a Lewis acid in the form of an inorganic halide salt.

3. A process in accordance with claim 1 wherein the Lewis acid used in forming said mixture is aluminum trichloride.

4. A process in accordance with claim 1 wherein the R groups of RSSR are the same.

5. A process in accordance with claim 4 wherein the R groups of RSSR each have up to about 10 carbon atoms.

6. A process in accordance with claim 1 wherein the disulfide used in forming said mixture is dimethyldisulfide.

7. A process in accordance with claim 6 wherein the mixture is heated at reflux temperature(s) at ordinary atmospheric pressure(s).

8. A process in accordance with claim 1 wherein said mixture is formed from at least 2 equivalents of Lewis acid per mole of the disulfide used in forming the mixture and wherein the molar ratio of benzene to said disulfide is at least 5:1.

9. A process which comprises heating a mixture formed from ingredients comprising (i) at least one disulfide of the formula RSSR where each R is, independently, an alkyl group having up to about 15 carbon atoms, (ii) benzene in an amount such that the molar ratio of benzene to said disulfide used in forming said mixture is at least about 5:1, and (iii) at least about 2 equivalents of Lewis acid per mole of the disulfide used in forming the mixture, at one or more temperatures effective to form a compound of the formula $RSC_6H_5$ where R is an alkyl group having up to about 15 carbon atoms, such that said compound of the formula $RSC_6H_5$ is formed.

10. A process in accordance with claim 9 wherein the Lewis acid used in forming said mixture is a Lewis acid in the form of an inorganic halide salt, and wherein the molar ratio of benzene to said disulfide used in forming said mixture is at least about 10:1.

11. A process in accordance with claim 10 wherein the Lewis acid used in forming said mixture is aluminum trichloride, and wherein the R groups of RSSR are the same.

12. A process in accordance with claim 11 wherein the R groups of RSSR each have up to about 10 carbon atoms.

13. A process in accordance with claim 10 wherein the mixture is heated at reflux temperature(s) at ordinary atmospheric pressure(s).

14. A process in accordance with claim 13 wherein the R groups of RSSR are the same alkyl groups.

15. A process in accordance with claim 9 wherein the molar ratio of benzene to said dialkyldisulfide used in forming said mixture is at least about 10:1 and wherein the R groups of RSSR are the same alkyl groups.

16. A process which comprises heating a mixture formed from ingredients consisting essentially of (i) dimethyldisulfide, (ii) benzene in an amount such that the molar ratio of benzene to dimethyldisulfide used in forming said mixture is at least about 5:1, and (iii) at least about 2 moles of a Lewis acid in the form of an inorganic halide salt per mole of the dimethyldisulfide used in forming the mixture, at one or more temperatures effective to form thioanisole, such that thioanisole is formed.

17. A process in accordance with claim 16 wherein the molar ratio of benzene to the dimethyldisulfide used in forming said mixture is at least about 10:1.

18. A process in accordance with claim 16 wherein the mixture is heated to reflux temperature(s) at ordinary atmospheric pressure(s).

19. A process in accordance with claim 16 wherein the Lewis acid used in forming said mixture is aluminum trichloride.

20. A process in accordance with claim 16 wherein the molar ratio of benzene to the dimethyldisulfide used in forming said mixture is at least about 10:1; wherein the Lewis acid used in forming said mixture is aluminum trichloride; and wherein the mixture is heated to reflux temperature(s) at ordinary atmospheric pressure(s).

* * * * *